United States Patent [19]

Burgoyne, Jr. et al.

[11] Patent Number: 4,845,283
[45] Date of Patent: Jul. 4, 1989

[54] ALKENYLATED DIPHENYLDIISOCYANATES FOR USE IN PREPARING POLYURETHANE/UREA SYSTEMS

[75] Inventors: William F. Burgoyne, Jr., Emmaus, Pa.; Dale D. Dixon, Venice, Fla.

[73] Assignee: Air Products and Chemicals, Inc., Allentown, Pa.

[21] Appl. No.: 108,408

[22] Filed: Oct. 14, 1987

[51] Int. Cl.$^4$ .................... C07C 118/00; C08G 18/00
[52] U.S. Cl. .................... 560/359; 521/163
[58] Field of Search ........................ 560/359

[56] References Cited

U.S. PATENT DOCUMENTS

| | | | |
|---|---|---|---|
| 2,786,864 | 3/1957 | Wirth et al. | 560/359 |
| 3,105,845 | 10/1963 | Fetterly | 260/453 |
| 3,180,883 | 4/1965 | Case | 260/453 |
| 3,878,235 | 4/1975 | Schnabel | 260/453 AM |
| 4,399,073 | 8/1983 | Schaefer | 260/453 |
| 4,440,871 | 4/1984 | Lok | 502/214 |
| 4,500,651 | 2/1985 | Lok | 502/208 |
| 4,551,236 | 11/1985 | Lok | 208/112 |
| 4,605,492 | 8/1986 | Lok | 208/310 Z |

FOREIGN PATENT DOCUMENTS 1080739 8/1967 United Kingdom .

*Primary Examiner*—Alan Siegel
*Attorney, Agent, or Firm*—Russell L. Brewer; James C. Simmons; William F. Marsh

[57] ABSTRACT

This invention relates to alkenylated diphenyldiisocyanates having at least one alkenyl group ortho to an isocyanate group. More particularly the diphenyldiisocyanates are represented by the formula:

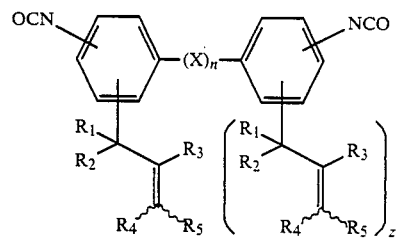

wherein $R_1$, $R_2$, $R_3$, $R_4$ and $R_5$ are hydrogen, $C_{1-3}$ aliphatic, phenyl, halogen or alkoxy radicals, or $R_2$ and $R_4$ or $R_5$ are bridged via an alkylene radical $-(CH_2)_y-$ wherein y=2 to 5 provided not more than one is phenyl, halogen, or alkoxy, X is methylene, alkylene, or branched $C_1$-$C_6$ alkylene group, oxygen, sulfur, carbonyl, sulfonyl or fluoroalkylene group, n is 0 or 1 and z is 0 or 1.

The above described alkenylated diphenyldiisocyanates have been found to be well suited for preparing crosslinkable condensation polymers by providing pendant unsaturation for post curing and polymerization. They are also well suited for preparing polyurethane and polyurea elastomer systems.

31 Claims, No Drawings

ALKENYLATED DIPHENYLDIISOCYANATES FOR USE IN PREPARING POLYURETHANE/UREA SYSTEMS

TECHNICAL FIELD

This invention pertains to alkenylated diphenyldiisocyanates having particular suitability for post curable, crosslinkable polyurethane/urea elastomer systems.

BACKGROUND OF THE INVENTION

Alkylated aromatic diisocyanates have been known for a substantial period of time and find use in the preparation of polyurethane and polyurea elastomers. The isocyanates are reacted with polyols to produce a polyurethane sysem which then can be crosslinked with an aromatic diamine to form a polyurethane/urea elastomer or crosslinked with a short chained diol or triol to produce polyurethane elastomers. Alkylated and substituted aromatic isocyanates which have found use in preparing various elastomer systems are noted in the following patents:

British Pat. No. 1,080,739 discloses alkylated mononuclear monoisocyanates and alkylated diphenyldiisocyanates. The isocyanates are characterized as containing a tertiary alkyl group in ortho positions to each isocyanate group to inhibit the reactivity of the isocyanate group. The reduced reactivity permits greater flexibility in carrying out reactions and the utilization of wider variety of reactants for producing elastomer systems. Examples of diphenylmethanediisocyanates having hindered groups include the isocyanate derivatives of 4,4'-methylene bis(2-tert-butylaniline) and 4,4'-methylene bis(2-methyl-6-tert-butylaniline).

U.S. Pat. No. 3,105,845 discloses the preparation of tetraalkylated mononuclear aromatic polyisocyanates and their use in producing a variety of elastomeric systems. One of the advantages of the alkylated mononuclear aromatic isocyanates is in their reduced reactivity and thus provides a more stable "pot life" for polymer intermediates. Examples of diisocyanates include 1,3,5-trimethyl-2,4-disocyanatobenzene; durene isocyanate and 1,3-dimethyl-2,5-diethyl-4,6-diisocyanatobenzene.

U.S. Pat. No. 4,399,073 discloses a process for producing tertiary alkyl isocyanates such as tetramethylxylenediisocyanate, 1,3,5-tris(1-isocyanato-1-methylethyl)benzene and α,α-dimethyl-4-isopropenylbenzeneisocyanate.

U.S. Pat. No. 3,878,235 discloses the production of chlorine-containing methylene-bridged diaryl diisocyanates and the use of these diisocyanates for the preparation of polyurethane elastomer systems. The chloro containing methylene bridged diphenyldiisocyanates have low viscosity and low volatility as compared to toluenediisocyanate for example thus reducing the toxicity problem associated with a mononuclear aromatic diisocyanate such as toluenediisocyanate. The orthochlorobenzyltoluenediisocyanate was shown to be a stable liquid under extended period of time as whereas the para-chlorobenzyl-toluenediisocyanate was not a stable liquid but exhibited partial solidification on standing.

U.S. Pat. No. 3,180,883 discloses 4,4'-diisocyanato-3,5-di-lower alkyl diphenylmethane compositions for use in preparing polyurethanes. Blocking groups are disclosed which inhibit the reactivity of one of the isocyanate groups, these blocking groups being halogen or alkyl.

SUMMARY OF THE INVENTION

This invention pertains to alkenylated diphenyldiisocyanates and derivatives thereof and particularly to monoalkenylated diphenylmethanediisocyanates. In contrast to prior art aromatic diisocyanate compositions, the organo group contains carbon-carbon unsaturation and is polymerizable with amine-reactive difunctional condensation monomers such as dicarboxylic acids and their esters, polyol and epoxy system and also in addition, polymerizable with other unsaturated monomer systems. These aromatic diisocyanate compositions are represented by the formula: wherein $R_1$, $R_2$, $R_3$, $R_4$ and $R_5$ are hydrogen, $C_{1-3}$ aliphatic, phenyl, halogen or alkoxy radicals, or $R_2$ and $R_4$ or $R_5$ are bridged via an alkylene radical $-(CH_2)_y-$ wherein $y=2$ to 5 provided not more than one is phenyl, halogen, or alkoxy, X is methylene, alkylene, or branched $C_1-C_6$ alkylene group, oxygen, sulfur, carbonyl, sulfonyl or fluoroalkylene group, n is 0 or 1 and z is 0 or 1.

There are several advantages associated with the specific compositions of this invention and these advantages include:
- a diphenyldiisocyanate composition which has at least one unsaturated organo group ortho to an isocyanate group, for providing reduced activity for at least one of the isocyanate groups which permits specialty type reactions;
- a diphenyldiisocyanate composition that provides for attachment of organic radicals or polymers at one or both nitrogens which allows for tailoring of the solubility characteristics;
- a diphenyldiisocyanate composition which has an unsaturated organo group ortho to an isocyanate for providing desirable reactivity for urethane and polyurea elastomer systems;
- alkenylated diphenyldiisocyanates having a carbon-carbon unsaturation for producing unique properties in polyurethane and polyurea resin systems, latexes, UV curable coatings and adhesives and as reactive diluents for polyesters;
- an ability to produce a variety of resin systems, e.g., polyurethane systems; and other condensation polymers such as polyamides, polyesters, and polyethers; and
- an ability to effect reaction between various resin systems and polymerizable monomers and thereby introduce monomer groups for desirable end properties.

DETAILED DESCRIPTION OF THE INVENTION

The compounds of this invention, as indicated above, are represented by the formulas:

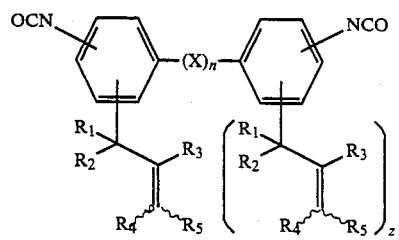

wherein $R_1$, $R_2$, $R_3$, $R_4$ and $R_5$ are hydrogen, $C_{1-3}$ aliphatic, phenyl, halogen or alkoxy radicals, or $R_2$ and $R_4$ or $R_5$ are bridged via an alkylene radical —$(CH_2)_y$— wherein y=2 to 5 provided not more than one is phenyl, halogen, or alkoxy, X is methylene, alkylene, or branched $C_1$-$C_6$ alkylene group, oxygen, sulfur, carbonyl, sulfonyl or fluoroalkylene group, n is 0 or 1 and z is 0 or 1.

The structural formula has been written to reflect that stereo chemistry exists in the reaction product and $R_5$ may be cis or trans to $R_3$. When $R_5$ is cis with $R_3$, then $R_4$ is combined with $R_2$ rather than $R_5$ being combined with $R_2$ in order to form a $\beta,\gamma$-unsaturated ring.

The compounds of this invention are synthesized by alkylating dianilines, e.g., 4,4'-methylenedianiline or 3,3'-methylenedianiline, 3,4'-methylenedianiline or oxydianilines. The diamine is then converted to the diisocyanate by conventional means. It is because the alkenylation is effected via the aromatic amine that one is able to introduce at least one alkenyl group in a position ortho to an amine group, or to both amine groups an hence to the isocyanate group and achieve unique results associated with the specific regiochemistry associated with those isomers. These unique properties include urethane processability characteristics.

Much of the art describing the manufacture of alkenylated aromatic hydrocarbons uses a homogenous catalyst system, e.g., boron trifluoride or boron trifluoride-phosphoric acid mixture or weakly acidic heterogenous catalyst systems. Other art in the manufacture of alkylated aromatic amines uses bleaching earths, clays, montmorillonite and alkali metal ion exchanged zeolites. In contrast to prior art methods for producing alkenylated phenols and alkylated aromatic amines, it is our belief the alkenylated aromatic amines are best prepared using silica-alumina or crystalline molecular sieves which are solid phase and have an acidity factor of at least 0.3 and preferably in excess of 0.8 as the catalyst. The acidity factor is a measurement of acidity of the zeolite catalyst and involves contact of the catalyst with ammonia under adsorption conditions followed by desorption. More particularly, one gram of catalyst is contacted with ammonia at room temperature and then desorbed by heating to a temperature from ambient to 200° C. at a rate of 10° per minute, then holding at 200° C. for two hours. The amount of ammonia irreversibly adsorbed by one gram at 200° C. is indicative of acidity and indicative of the strength of the amine/acid bond. The acidity factor then is the amount of ammonia irreversibly adsorbed expressed in millimoles per gram of catalyst at 200° C. and as stated this level should be at least 0.3 and preferably 0.8 millimoles ammonia per gram of catalyst.

Zeolites which can be utilized for alkenylation of diphenylmethane diamine include X, Y, faujasite, ferrierite, offretite, chabazite, gmelinite, erionite, ferrierite, mordenite and the ZSM family. When initially prepared, the cation in the crystalline molecular sieve is an alkali metal, typically sodium. This ion must be exchanged in sufficient proportion, usually, 60% or greater, with an acidic ion such as a rare earth metal, e.g., lanthanum, praseodymium; hydrogen or some of the transition metals such as nickel, copper, chromium and the like. The substitution of various ions for the sodium ion alters the acidity of crystalline molecular sieve, thus making it more reactive and catalytically effective for ring alkenylation of the aromatic amine.

The naturally occurring and synthetic zeolites used in the process normally have a silica to alumina molar ratio from about 2 to 25:1. However, if the silica to alumina ratio is low or acidity borders on the low side of that desired, the silica to alumina ratio and acidity of the zeolite may be altered by a technique called dealumination. In effect, the practice of dealumination decreases the alumina content in the zeolite thereby increasing the silica to alumina ratio. The removal of alumina from the internal structure affects acidity and may also enlarge the cage structure or pore size of the zeolite to permit entry of and diffusion of larger molecules into its internal structure. Thus, one may be able to utilize a particular cation in a dealuminated zeolite, but not use the same cation in its non-dealuminated state. This is because the original cation may not have provided sufficient acidity for effecting ring alkenylation. Some of the techniques for dealumination include chelation, dehydration or acidification, the latter entailing the treatment of the zeolite with an inorganic acid. Techniques suited for dealumination of zeolites are well known.

Zeolites and crystalline molecular sieves are porous materials with the pores having generally uniform molecular dimensions. Cavities or cages are formed in this zeolite or molecular sieve and connected by channels of generally defined diameter. For the practice of this invention the pore diameter should be sufficiently large to permit the molecules to effectively enter the interior of the molecular sieve for reaction and to exit as final product. Typically, the pore size will range from about 6 to 15 Angstroms, but the size of a pore required for reaction can vary depending upon the product being produced. If conversion levels appear low for the particular catalyst, that level may be due to reactant diffusion resistance through the molecular sieve. If that is the case, a molecular sieve of slightly larger pore size should be tried.

Molecular sieves have been developed which have been defined as nonzeolites but have a cage structure that performs similarly to zeolites. In many cases, they contain alumina and silica in combination with other components, e.g., phosphorus, boron, germanium, titanium, etc. In the alkenylation of 4,4'-methylenedianiline as described here, they perform similarly to zeolites, and representative crystalline molecular sieves are described in U.S. Pat. No. 4,440,871; European Pat. No. 124,119 and European Pat. No. 121,232 and the subject matter of these patents incorporated by reference. Borosilicate and borogermanate zeolites, although not disclosed in these patents, possibly can also be used. For purposes of forming alkenylated toluenediamines and their subsequent conversion to diisocyanates molecular sieves are deemed equivalent to and included as catalyst material.

Diolefins useful in this invention are acyclic and cyclic conjugated dienes. Examples of some dienes are 1,3-butadiene, isoprene, chloroprene, 2,3-dimethyl-1,3-butadiene, piperylene, 2-methyl-1,3-pentadiene, 2,4-hexadiene, 3,4-dimethyl-2,4-hexadiene, 2-phenyl-1,3-butadiene, 2-methoxy-1,3-butadiene, 2,5-dimethyl-2,4-hexadiene, cyclopentadiene, dicyclopentadiene, methylcyclopentadiene and 1,4-cyclooctadiene.

The aromatic diamine compositions which can be converted to preferred alkenylated diisocyanates are listed below. Again z may be 0 or 1.

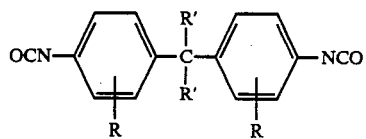

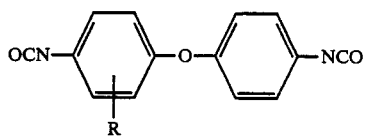

wherein R = —CH$_2$CH=CH$_3$
= —CH$_2$CH=C(CH$_3$)$_2$
= —C(CH$_3$)CH=CH$_2$
= —C(CH$_3$)$_2$CH=C(CH$_3$)

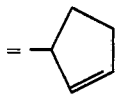

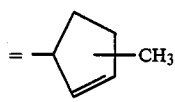

Ring alkenylation is effected by reacting the diamine with the diolefin at temperatures ranging from about 100° to 250° C. and preferably from about 140° to 220° C. The pressures will range from about 15 to 2000 psig and generally in the range of 100 to 1000 psig. It is common practice to alter the temperature and the pressure within the above ranges specified to optimize selectivity and conversion to the desired product. Mole ratios of olefin to diamine used in the reaction will range from about 1:5 to 10:1 and the reaction time will generally be from about 2 to 48 hours when synthesized in an autoclave or within 0.05 to 6 hr$^{-1}$, expressed as a liquid hourly space velocity (LHSV) for fixed bed continuous operation.

Alternatively, alkenylated diphenylmethane diisocyanates, such as 4,4′-diphenylmethanediisocyanate, may be prepared by ortho-alkenylation of aniline or substituted derivatives, followed by coupling with formaldehyde and subsequent phosgenation as shown below for a synthesis procedure using dicyclopentadiene.

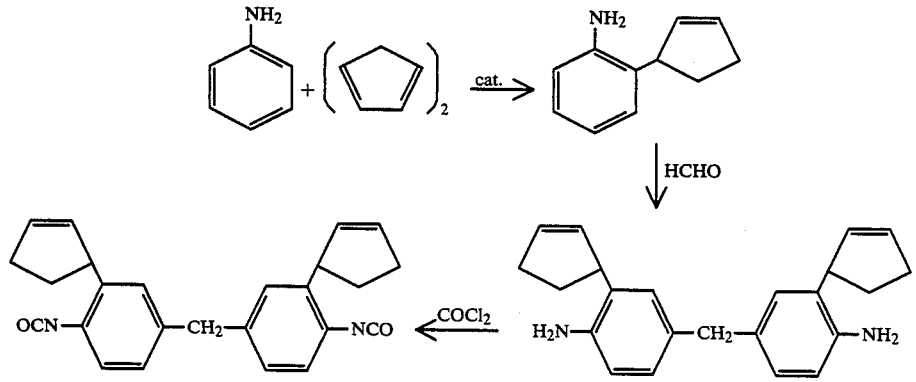

In the ring alkenylation of aniline and methylene dianilines utilizing the solid acid catalyst systems, the diolefins, and particularly the olefins having conjugated unsaturation, tend to polymerize and generate substantial amounts of by-product polymer. In many cases the combination of reactant and catalyst preclude the formation of alkenylated dianilines and substantially all of the olefin is converted to by-product polymer. Butadiene and cyclopentadiene are two offenders and both polymerize readily under the reaction conditions providing low yields of ring alkenylation. To avoid polymer production it is necessary to carry out the ring alkenylation of aryldiamine in the presence of a solvent which is inert to reaction with aryldiamine or the olefin and does not promote polymerization. Solvents include paraffins such as pentane, hexane, heptane, octane, decane; toluene and xylene, paraffinic naptha fractions, kerosene; and cycloparaffin hydrocarbons having from about 5 to 10 carbon atoms, e.g., cyclohexane and so forth other inert solvents, especially ethers such as dioxane and tetrahydrofuran may be effectively used.

The major problem in forming the alkenylated diphenyldiisocyanate is in the formation of the alkenylated dianiline intermediate. Once the intermediate is formed, that intermediate can be converted to the isocyanate group by the conventional technique of phosgenation. Typically this will involve contacting the alkenylated diisocyanate in an aromatic solvent with a phosgene solution at temperatures below about 60° C. Additional phosgene may be injected into the reaction mixture as required until reaction is complete. The final solution of reaction product then is fractionated by removing hydrogen chloride and unreacted phosgene and solvent and recovering the alkenylated diphenylmethane diisocyanate residue.

The alkenylated diphenyldiisocyanates described herein have a variety of uses and can be used in preparing coatings and adhesives. In contrast to currently available urethane coating systems having unsaturation therein, e.g. those containing glycerides of linseed oil or other siccative oil in an isocyanate prepolymer backbone, the unsaturation is pendant from the backbone. When the unsaturation is in the polymer backbone, as in the prior art, one may experience difficulty in obtaining desirable polymerization rates and in obtaining desirable rates for post curing of the reactive unsaturation. With the alkenylated diphenyldiisocyanate, the unsaturation is pendant from the polymer backbone and permits faster post curing while still providing a desirable aromatic ring in the backbone.

The text, *Polyurethanes Chemistry and Technology* by Saunders and Frisch, (1964) has several chapters relating to the utilization of polyurethanes having unsaturation therein; such chapters include applications for coatings, adhesives, and fibers.

In addition to formulating polyurethanes or polyurea elastomers, the pendant unsaturation in the alkenylated diphenyldiisocyanates can be polymerized by conventional techniques with other polymerizable monomers, to enhance the physical properties of the elastomers systems. Typical monomers which may be polymerized with the pendant unsaturation include vinyl acetate, lower alkyl ($C_{1-6}$) esters of acrylic and methacrylic acid, vinyl chloride, vinylidine chloride, styrene, butadiene, isoprene, and cyclopentadiene.

One of the problems associated with effecting polymerization of the alkenylated diisocyantes with other polymerizable monomers is the relatively slow polymerization activity of the alkenylated diisocyanates. During alkenylation, the residual double bond becomes allylic to the aromatic ring. As is known, the reactivity of the allylic double bond is low and catalyst levels and conditions may require adjustment to obtain desirable polymerization rates. The bond may be isomerized to a conjugated relationship with the ring.

The following examples are provided to illustrate preferred embodiments of the invention and are not intended to restrict the scope thereof. All parts are part by weight and all percentages are expressed as weight percent unless otherwise specified.

EXAMPLE 1

Preparation of
2-(cyclopent-2-enyl)-4,4'-methylenedianiline

A 1.64 mol portion of 4,4'-methylenedianiline, 1.23 mol (2.45 equivalent) of dicyclopentadiene, 2.78 mol of pentane, and 20.0 g of an amorphous silica-alumina catalyst comprised of 13% alumina and 87% silica were charged to a 1000 cc pressure vessel equipped with a mechanical stirrer. The vessel was sealed and purged with nitrogen leaving a 32 psig nitrogen blanket. The vessel contents were heated to 205° C. with stirring and were maintained at that temperature for 22 hr. The contents were cooled to 150° C. and isolated catalyst free by hot filtration. Selective removal of residual hydrocarbons by vacuum distillation and analysis by gas chromatography (GC) revealed the following product mixture:

|  | GC Area % |
|---|---|
| 4,4'-methylene dianiline | 34% |
| 2-(cyclopent-2-enyl)-4,4'-methylene dianiline | 59% |
| Other Aromatic Diamine derivatives | 7% |
|  | 100.0% |

EXAMPLE 2

Preparation of
2-(cyclopent-2-enyl)-4,4'-diphenylmethane diisocyanate

A solution of 0.40 mol of 2-(cyclopent-2-enyl)-4,4'-methylene dianiline in 1000 cc of dioxane was added dropwise to 98 cc (0.82 mol) of diphosgene contained in a 2 L round-bottomed flask. The addition was carried out over approximately 1.5 hours, resulting in the formation of a precipitate. The temperature of the reaction mixture increased to 38° C. Upon completion of addition, the slurry was heated to 57° C. and stirred at that temperature for two hours. As the mixture warmed to 50° C. the thick slurry turned to a clear homogeneous liquid. After stirring at 57° C. for two hours, the mix was heated to 85° C. and maintained at that temperature for four hours. The solvent was then removed by distillation. The residual dark brown liquid was isolated by bulb-to-bulb vacuum distillation, affording a 65% yield of a light yellow liquid. The product structure was verified by gc/ms, IR and 'HNMR analysis.

EXAMPLE 3

Air Curing of a Polymer Containing
Alkenylmethylenediphenyldiisocyanate (a) Preparation of the Polyurethane:

2.5 g of the diisocyanate of Example 2 is added to a single neck 100 cc round bottom flask containing 25 g of tetrahydrofuran. A one-half molar equivalent of triethylene glycol is added followed by two drops of triethylamine. After the mix is stirred overnight, a molar equivalent of dodecanol is added and the mixture stirred for an additional 1.5 hours. The tetrahydrofuran is then removed on a rotary evaporator and any further amounts of tetrahydrofuran can be removed by exposure of the residue to high vacuum (0.01 mm) for three hours. A polyurethane product is obtained.

(b) Air Curing Experiments:

The polyurethane product desired above is mixed with several drops of cobalt napthenate solution and spread as a film on a glass plate. After 1.5 hours at room temperature, the polyurethane film based is hard and brittle while a film based on toluenediisocyanate is an unchanged gum. However, over a period of several days a film which is based on 2,4-toluenediisocyanate will also harden.

What is claimed is:

1. A diphenyldiisocyanate composition having at least one alkenyl substituent ortho to an isocyanate group represented by the formula:

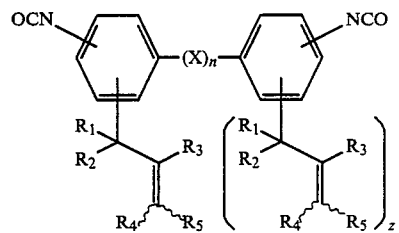

wherein $R_1$, $R_2$, $R_3$, $R_4$ and $R_5$ are hydrogen, $C_{1-3}$ aliphatic, phenyl, halogen or alkoxy radicals, or $R_2$ and $R_4$ or $R_5$ are bridged via an alkylene radical —$(CH_2)_y$— wherein y=2 to 5 provided not more than one is phenyl, halogen, or alkoxy, X is [methylene, alkylene, or branched] a $C_{1-6}$ alkylene group, oxygen, sulfur, carbonyl, sulfonyl or fluoroalkylene group, n is 0 or 1 and z is 0 or 1.

2. The composition of claim 1 wherein X is $CH_2$, n is 1 and z is 0.

3. The composition of claim 2 wherein $R_1$, $R_2$, $R_3$, and $R_4$ are hydrogen and $R_5$ is $C_1$ aliphatic.

4. The composition of claim 2 wherein $R_1$, $R_2$, and $R_3$ are hydrogen and $R_4$ and $R_5$ are $C_1$ aliphatic.

5. The composition of claim 1 wherein $R_1$, $R_2$, $R_3$ and $R_4$ are hydrogen, $R_5$ is $C_1$ aliphatic and z is 1.

6. The composition of claim 2 wherin $R_1$, and $R_4$ are hydrogen and $R_2$, $R_3$ and $R_5$ are $C_1$ aliphatic.

7. The composition of claim 2 wherein $R_2$, $R_3$ and $R_4$ are hydrogen and $R_1$ and $R_5$ are $C_1$ aliphatic.

8. The composition of claim 2 wherein $R_1$, and $R_3$ are hydrogen and $R_2$, $R_4$ and $R_5$ are $C_1$ aliphatic.

9. The composition of claim 2 wherein $R_2$ and $R_3$ are hydrogen and $R_1$ and $R_4$ are $C_1$ and $R_5$ is $C_2$ aliphatic.

10. The composition of claim 2 wherein $R_1$, $R_2$, $R_3$ and $R_4$ are $C_1$ aliphatic and $R_5$ is $C_2$ aliphatic.

11. The composition of claim 2 wherein $R_1$ and $R_2$ are $C_1$ aliphatic and $R_3$, $R_4$, and $R_5$ are hydrogen.

12. The composition of claim 1 wherein X is $CH_2$, $R_1$, $R_3$ and $R_4$ are hydrogen and $R_2$ and $R_5$ are a $C_1$ aliphatic and Z is 1.

13. The composition of claim 1 wherein X is $CH_2$, $R_1$ and $R_3$ are hydrogen, $R_2$, $R_4$ and $R_5$ is $C_1$ aliphatic and z is 1.

14. The composition of claim 2 wherein $R_3$ and $R_4$ are hydrogen, $R_1$ and $R_2$ are $C_1$ aliphatic and $R_5$ is a $C_3$ branched aliphatic.

15. The composition of claim 2 wherein $R_1$, $R_3$ and $R_4$ are hydrogen and $R_2$ and $R_5$ are combined to form a 5 carbon membered ring.

16. The composition of claim 1 wherein X is $CH_2$, $R_1$ and $R_3$ are hydrogen, $R_4$ is $C_1$ aliphatic, $R_2$ and $R_5$ are combined to form a 5 carbon membered ring and Z is 1.

17. The diphenylmethanediisocyanate of claim 1 wherein X is oxygen, n is 1 and z is 0.

18. The composition of claim 17 wherein $R_1$, $R_2$, $R_3$, and $R_4$ are hydrogen and $R_5$ is $C_1$ aliphatic.

19. The composition of claim 17 wherein $R_1$, $R_2$, and $R_3$ are hydrogen and $R_4$ and $R_5$ are $C_1$ aliphatic.

20. The composition of claim 1 wherein X is oxygen, $R_1$, $R_2$, $R_3$ and $R_4$ are hydrogen, $R_5$ is $C_1$ aliphatic and z is 1.

21. The composition of claim 17 wherein $R_1$ and $R_4$ are hydrogen and $R_2$, $R_3$ and $R_5$ are $C_1$ aliphatic.

22. The composition of claim 17 wherein $R_2$, $R_3$ and $R_4$ are hydrogen and $R_1$ and $R_5$ are $C_1$ aliphatic.

23. The composition of claim 17 wherein $R_1$, and $R_3$ are hydrogen and $R_2$, $R_4$ and $R_5$ are $C_1$ aliphatic.

24. The composition of claim 17 wherein $R_2$ and $R_3$ are hydrogen, $R_1$ and $R_4$ are $C_1$ and $R_5$ is $C_2$ aliphatic.

25. The composition of claim 17 wherein $R_1$, $R_2$, $R_3$ and $R_4$ are $C_1$ aliphatic and $R_5$ is $C_2$ aliphatic.

26. The composition of claim 17 wherein $R_1$, $R_3$ and $R_4$ are hydrogen and $R_2$ and $R_5$ represents a five carbon membered ring.

27. The composition of claim 1 wherein X is oxygen, $R_1$ and $R_2$ are $C_1$ aliphatic, $R_3$, $R_4$ and $R_5$ are hydrogen and z is 1.

28. The composition of claim 1 wherein X is oxygen, $R_1$ and $R_3$ are hydrogen, $R_2$, $R_4$ and $R_5$ are $C_1$ aliphatic and z is 1.

29. The composition of claim 17 wherein $R_3$ and $R_4$ are hydrogen, $R_1$ and $R_2$ are $C_1$ aliphatic and $R_5$ is a $C_3$ branched aliphatic.

30. The composition of claim 17 wherein $R_1$, $R_3$ and $R_4$ are hydrogen and $R_2$ and $R_5$ are combined to form a 5 carbon membered ring.

31. The composition of claim 1 wherein X is oxygen, $R_1$ and $R_3$ are hydrogen, $R_4$ is $C_1$ aliphatic and $R_2$ and $R_5$ are combined to form a 5 carbon membered ring and Z is 1.

* * * * *